United States Patent [19]

Bernasconi et al.

[11] Patent Number: 5,633,437
[45] Date of Patent: May 27, 1997

[54] GENE EXHIBITING RESISTANCE TO ACETOLACTATE SYNTHASE INHIBITOR HERBICIDES

[75] Inventors: Paul Bernasconi, Morgan Hill; Alison R. Woodworth, Palo Alto, both of Calif.

[73] Assignee: Sandoz Ltd., Basel, Switzerland

[21] Appl. No.: 321,356

[22] Filed: Oct. 11, 1994

[51] Int. Cl.$^6$ ............... C12N 15/52; C12N 15/82; C12N 15/29; A01H 1/00; A01H 5/00
[52] U.S. Cl. ............... 800/205; 435/172.3; 435/320.1; 435/418; 536/23.1; 536/23.2; 536/23.6; 800/DIG. 56
[58] Field of Search ............... 800/205, DIG. 56; 536/23.1–23.74; 435/172.3, 320.1, 240.4, 6

[56] References Cited

U.S. PATENT DOCUMENTS 5,013,659  5/1991  Bedbrook et al. ............... 435/172.3
5,231,020  7/1993  Jorgensen et al. ............... 800/205

FOREIGN PATENT DOCUMENTS 525384  2/1993  European Pat. Off. ........ C12N 15/60

OTHER PUBLICATIONS

Lee et al. (1988) "The molecular basis of sulfonylurea herbicide resistance in Tobacco" EMBO J. 7:1241–1248.
Sathasivan et al. (1991) "Molecular basis of imidazolinone herbicide resistance in Arabidopsis Thaliana va Colombia" Plant Physiol. 97:1044–1050.

*Primary Examiner*—David T. Fox
*Assistant Examiner*—Thomas Haas
*Attorney, Agent, or Firm*—Lynn Marcus-Wyner; Michael P. Morris

[57] ABSTRACT

The present invention provides a novel gene and enzyme isolated from cocklebur (Xanthium sp.) which confers resistance to several structurally unrelated classes of herbicides in plants, plant tissues and seeds. In particular, the class of herbicides consists of herbicides wherein acetolactate synthase (ALS) is the site of action and includes sulfonylureas, imidazolinones, triazolopyrimidines, pyrimidyloxybenzoates and phthalides.

18 Claims, 12 Drawing Sheets

| Fig. 1A |
|---------|
| Fig. 1B |
| Fig. 1C |

```
  1   GAACAACAGC CACATGTTTC TGGACCATCG TCGTTCACAC CTATTTTAAT
 51   CAGATAAACA AAGTACAAAC ATAACATAAC ATAACCCTAG TACATAACAC
101   ACATTCAACA ATGGCGGCCA TCCCTCATAC AAACCCTTCC ATCACCACCA
151   AACCACCCTC ATCTCCACCA CGTCCCACCT TCCTCGCCCG TTTCACATTC
201   CCAATAACCT CCACTTCCCA TAAACGACAC CGTCTCCACA TCTCCAACGT
251   CCTCTCCGAC TCCAAACCCA CCATCACCCA TTCACCATTA CCAACCGAAT
301   CATTTATCTC CCGTTACGCT CCAGACCAAC CAAGAAAAGG CGCTGATGTT
351   CTCGTCGAAG CTCTGGAACG TGAAGGCGTT ACAGACGTCT TCGCTTACCC
401   AGGTGGTGCC TCCATGGAGA TCCACCAAGC TCTCACGCGC TCAACCACCA
451   TCCGCAACGT TCTCCCACGT CACGAACAGG GCGGCGTCTT TGCTGCCGAA
501   GGCTACGCAC GTGCCTCCGG TCTTCCCGGC GTCTGTATTG CAACCTCTGG
551   TCCTGGAGCT ACGAACCTAG TAAGTGGTCT TGCTGATGCT TTATTAGACA
601   GTGTTCCAAT GGTTGCTATT ACTGGTCAAG TTCCAGGAG AATGATTGGA
651   ACAGATGCGT TCAAGAAAC CCTATTGTT GAGGTAACAC GTTCCATTAC
701   TAAGCATAAT TATTTAGTTT TGGATGTCGA GGATATTCCC AGGATTGTTA
751   GGGAAGCTTT TTATCTTGCG TCTTCTGGTC GACCCGGACC GGTTTTAATT
```

FIG. 1A

```
 801  GATGTACCTA AGGATATACA GCAGCAGTTG GTAGTGCCTA AATGGGATGA
 851  GCCTATTAGG TTACCTGGGT ATTTGTCTAG GTTGCCTAAA ACGGAGAATA
 901  ATGGGCAGTT GGAACACATT GTTAGGTTGG TGAGTGAGGC CAAGAGGCCG
 951  GTTTTGTATG TGGGGGGTGG GTGTTTGAAT TCGGGAGATG AGTTGAGGCG
1001  GTTTGTGGAG CTTACGGGGA TACCGGTTGC GAGTACGTTG ATGGGCTTG
1051  GAGCGTACCC TGCTTCTAGT GATTTGTCGC TGCATATGCT TGGGATGCAT
1101  GGGACGGTTT ATGCGAATTA TGCGGTTGAT AAGAGTGATT TGTTGCTTGC
1151  GTTTGGGGTA AGGTTTGATG ACCGTGTGAC GGGGAAGCTT GAGGCTTTTG
1201  CTAGCAGAGC TAAGATTGTT CATATTGATA TTGATTCTGC GGAAATTGGG
1251  AAGAATAAGC AGCCTCATGT GTCGATTTGT GGTGATATCA AGGTCGCGTT
1301  ACAGGGTCTG AACAAGATTT TGGAGGTAAA GAATTCGGTG ACTAATCTTG
1351  ATTTCTCGAA CTGGAGGAAG GAATTGGATG AGCAAAAGGT TAAGTATCCG
1401  TTGAGTTTTA AAACATTTGG CGAAGCTATT CCTCCGCAGT ATGCCATTCA
1451  AGTGCTTGAT GAGTTAACGG GTGGGAATGC GATTATTAGC ACTGGGGTCG
1501  GGCAGCATCA GATGTGGGCT GCTCAGTTTT ACAAATACAA CAAGCCTAGA
1551  CAATGGCTGA CGTCAGGTGG ACTAGGCGCG ATGGGTTTTG GGTTGCCCGC
1601  TGCTATCGGG GCGGCTGTTG CAAGACCTGA TGCGGTAGTA GTTGATATCG
1651  ATGGTGATGG AAGCTTTATA ATGAGCGTTC AAGAGTTAGC CACAATCCGT
1701  GTTGAAAATC TTCCTGTTAA GATTTTGTTA CTTAACAATC AGCATTTGGG
1751  TATGGTGGTT CAGTTGGAGG ATCGGTTTTA CAAGGCGAAT CGGGCTCATA
```

FIG. 1B

```
1801  CCTACTTAGG AAATCCGTCA AAAGAGTCTG AAATATTCCC TAACATGTTG

1851  AAGTTTGCTG AAGCGTGTGA TATCCCAGCT GCCCGAGTGA CCCGGAAGGC

1901  AGATCTACGA GCAGCTATTC AGAAGATGTT GGATACACCG GGGCCTTACT

1951  TGTTGGATGT GATCGTGCCC CATCAAGAAC ATGTGTTGCC CATGATCCCG

2001  GCTGGTGGAG GTTTCATGGA TGTGATCACC GAAGGCGACG GCAGAATGAA

2051  ATATTGAGCT TCAATGTCAC ATATAGTGTG TTCTGTAAGC AGTTTGTCGG

2101  TTATGAAGTT AAATGTTTTG TTGTGTAATT TCGTTCCTGG TTAAAAAATC

2151  AAGCTT
```

FIG. 1C

MAAIPHTNPSITTKPPSSPPRPTFLARFTFPITSTSHKRHRLHISNVLSDSKPTI
THSPLPTESFISRYAPDQPRKGADVLVEALEREGVTDVFAYPGGASMEIHQALTR
STTIRNVLPRHEQGGVFAAEGYARASGLPGVCIATSGPGATNLVSGLADALLDSV
PMVAITGQVPRRMIGTDAFQETPIVEVTRSITKHNYLVLDVEDIPRIVREAFYLA
SSGRPGPVLIDVPKDIQQQLVVPKWDEPIRLPGYLSRLPKTENNGQLEHIVRLVS
EAKRPVLYVGGGCLNSGDELRRFVELTGIPVASTLMGLGAYPASSDLSLHMLGMH
GTVYANYAVDKSDLLLAFGVRFDDRVTGKLEAFASRAKIVHIDIDSAEIGKNKQP
HVSICGDIKVALQGLNKILEVKNSVTNLDFSNWRKELDEQKVKYPLSFKTFGEAI
PPQYAIQVLDELTGGNAIISTGVGQHQMWAAQFYKYNKPRQWLTSGGLGAMGFGL
PAAIGAAVARPDAVVVDIDGDGSFIMSVQELATIRVENLPVKILLLNNQHLGMVV
QLEDRFYKANRAHTYLGNPSKESEIFPNMLKFAEACDIPAARVTRKADLRAAIQK
MLDTPGPYLLDVIVPHQEHVLPMIPAGGGFMDVITEGDGRMKY

FIG. 2

| FIG. 3A |
|---|
| FIG. 3B |
| FIG. 3C |

```
  1    GAACAACAGC CACATGTTTC TGGACCATCG TCGTTCACAC CTATTTTAAT

51    CAGATAAACA AAGTACAAAC ATAACATAAC ATAACCCTAG TACATAACAC

101    ACATTCAACA ATGGCGGCCA TCCCTCATAC AAACCCTTCC ATCACCACCA

151    AACCACCCTC ATCTCCACCA CGTCCCACCT TCCTCGCCCG TTTCACATTC

201    CCAATAACCT CCACTTCCCA TAAACGACAC CGTCTCCACA TCTCCAACGT

251    CCTCTCCGAC TCCAAACCCA CCATCACCCA TTCACCATTA CCAACCGAAT

301    CATTTATCTC CCGTTACGCT CCAGACCAAC CAAGAAAAGG CGCTGATGTT

351    CTCGTCGAAG CTCTGGAACG TGAAGGCGTT ACAGACGTCT TCGCTTACCC

401    AGGTGGTGCC TCCATGGAGA TCCACCAAGC TCTCACGCGC TCAACCACCA

451    TCCGCAACGT TCTCCCACGT CACGAACAGG GCGGCGTCTT TGCTGCCGAA

501    GGCTACGCAC GTGCCTCCGG TCTTCCCGGC GTCTGTATTG CAACCTCTGG

551    TCCTGGAGCT ACGAACCTAG TAAGTGGTCT TGCTGATGCT TTATTAGACA

601    GTGTTCCAAT GGTTGCTATT ACTGGTCAAG TTCCCAGGAG AATGATTGGA

651    ACAGATGCGT TCAAGAAAC CCCTATTGTT GAGGTAACAC GTTCCATTAC

701    TAAGCATAAT TATTTAGTTT TGGATGTCGA GGATATTCCC AGGATTGTTA

751    GGGAAGCTTT TTATCTTGCG TCTTCTGGTC GACCCGGACC GGTTTTAATT
```

FIG. 3A

```
 801   GATGTACCTA AGGATATACA GCAGCAGTTG GTAGTGCCTA AATGGGATGA
 851   GCCTATTAGG TTACCTGGGT ATTTGTCTAG GTTGCCTAAA ACGGAGAATA
 901   ATGGGCAGTT GGAACACATT GTTAGGTTGG TGAGTGAGGC CAAGAGGCCG
 951   GTTTTGTATG TGGGGGGTGG GTGTTTGAAT TCGGAGATG AGTTGAGGCG
1001   GTTTGTGGAG CTTACGGGA TACCGGTTGC GAGTACGTTG ATGGGCTTG
1051   GAGCGTACCC TGCTTCTAGT GATTTGTCGC TGCATATGCT TGGGATGCAT
1101   GGGACGGTTT ATGCGAATTA TGCGGTTGAT AAGAGTGATT TGTTGCTTGC
1151   GTTTGGGGTA AGGTTTGATG ACCGTGTGAC GGGGAAGCTT GAGGCTTTTG
1201   CTAGCAGAGC TAAGATTGTT CATATTGATA TTGATTCTGC GGAAATTGGG
1251   AAGAATAAGC AGCCTCATGT GTCGATTTGT GGTGATATCA AGGTCGCGTT
1301   ACAGGGTCTG AACAAGATTT GGAGGTAAA GAATTCGGTG ACTAATCTTG
1351   ATTTCTCGAA CTGGAGGAAG GAATTGGATG AGCAAAAGGT TAAGTATCCG
1401   TTGAGTTTTA AAACATTTGG CGAAGCTATT CCTCCGCAGT ATGCCATTCA
1451   AGTGCTTGAT GAGTTAACGG GTGGGAATGC GATTATTAGC ACTGGGGTCG
1501   GGCAGCATCA GATGTGGGCT GCTCAGTTTT ACAAATACAA CAAGCCTAGA
1551   CAATGGCTGA CGTCAGGTGG ACTAGGCGCG ATGGGTTTTG GGTTGCCCGC
1601   TGCTATCGGG GCGGCTGTTG CAAGACCTGA TGCGGTAGTA GTTGATATCG
1651   ATGGTGATGG AAGCTTTATA ATGAGCGTTC AAGAGTTAGC CACAATCCGT
1701   GTTGAAAATC TTCCTGTTAA GATTTTGTTA CTTAACAATC AGCATTTGGG
```

FIG. 3B

```
1751   TATGGTGGTT CAGTTGGAGG ATCGGTTTTA CAAGGCGAAT CGGGCTCATA
1801   CCTACTTAGG AAATCCGTCA AAAGAGTCTG AAATATTCCC TAACATGTTG
1851   AAGTTTGCTG AAGCGTGTGA TATCCCAGCT GCCCGAGTGA CCCGGAAGGC
1901   AGATCTACGA GCAGCTATTC AGAAGATGTT GGATACACCG GGGCCTTACT
1951   TGTTGGATGT GATCGTGCCC CATCAAGAAC ATGTGTTGCC CATGATCCCG
2001   GCTGGTGGAG GTTTCATGGA TGTGATCACC GAAGGCGACG GCAGAATGAA
2051   ATATTGAGCT TCAATGTCAC ATATAGTGTG TTCTGTAAGC AGTTTGTCGG
2101   TTATGAAGTT AAATGTTTTG TTGTGTAATT CGTTCCTGG TTAAAAAATC
2151   AAGCTT
```

FIG. 3C

```
MAAIPHTNPSITTKPPSSPPRPTFLARFTFPITSTSHKRHRLHISNVLSDSKPTI
THSPLPTKSFISRYAPDQPRKGADVLVEALEREGVTDVFAYPGGASMEIHQALTR
STTIRNVLPRHEQGGVFAAEGYARASGLPGVCIATSGPGATNLVSGLADALLDSV
PMVAITGQVPRRMIGTDAFQETPIVEVTRSITKHNYLVLDVEDIPRIVREAFYLA
SSGRPGPVLIDVPKDIQQQLVVPKWDEPIRLPGYLSRFPKTENNGQLEQIVRLVS
EAKRPVLYVGGGCLNSGDELRRFVELTGIPVASTLMGLGAYPASSDLSLHMLGMH
GTVYANYAVDKSDLLLAFGVRFDDRVTGKLEAFASRAKIVHIDIDSAEIGKNKQP
HVSICGDIKVALQGLNKILEVKNSVTNLDFSNWRKELDEQKVKYPLSFKTFGEAI
PPQYAIQVLDELTGGNAIISTGVGQHQMWAAQFYKYNKPRQWLTSGGLGAMGFGL
PAAIGAAVARPDAVVVDIDGDGSFIMNVQELATIRVENLPVKILLLNNQHLGMVV
QWEDRFYKANRAHTYLGNPSKESEIFPNMLKFAEACDIPAARVTRKADLRAAIQK
MLDTPGPYLLDVIVPHQEHVLPMIPAGGGFMDVITEGDGRMKY
```

FIG. 4

GENE EXHIBITING RESISTANCE TO ACETOLACTATE SYNTHASE INHIBITOR HERBICIDES

FIELD OF THE INVENTION

This invention relates to a novel gene and enzyme isolated from cocklebur (Xanthium sp.) which confers resistance to several structurally unrelated classes of herbicides in plants, plant tissues and seeds. In particular, the class of herbicides consists of herbicides wherein acetolactate synthase (ALS) is the site of action and includes sulfonylureas, imidazolinones, triazolopyrimidines, pyrimidyloxybenzoates and phthalides.

BACKGROUND OF THE INVENTION

The control of undesirable plants by the use of herbicides is an extensively used practice and the market for herbicidal compounds continues to expand. However, some weedy plant species are resistant to some of these herbicidal compounds. As a result, either greater amounts of the herbicidal compounds must be applied to control these weeds, or herbicides with greater potency have to be used. The result in either case can frequently be a sensitivity of desirable crop plants to the herbicidal compounds. An alternative to the use of increased amounts of herbicides or the application or identification and development of new herbicides for use with particular crop plants is the modification of susceptible or sensitive crop species so that they are resistant or tolerant to specific herbicides. This strategy of modifying susceptible or sensitive crop species should reduce chemical herbicide input while at the same time maximizing weed control. A number of methods exist for achieving this goal, and one such method is through the genetic transformation of crop plants for herbicide resistance.

Resistance to specific herbicides has been shown to be the result of changes in enzymes which are involved in particular biosynthetic pathways. For example, the non-selective postemergence herbicide glyphosate acts by inhibiting the enzyme 5-enolpyruvyl-3-phosphoshikimate synthase (EPSP). Glyphosate tolerant plants have been produced by inserting into the genome of a plant the capacity to produce high levels of EPSP synthase and reference is made to U.S. Pat. No. 5,312,910. Also glyphosate tolerant plants have been produced by desensitizing EPSP synthase to glyphosate.

Acetolactate synthase (ALS) which catalyzes the first reaction in the biosynthetic pathway to the branched amino acids has been shown to be the site of action of several structurally unrelated classes of herbicides, including: sulfonylureas (LaRossa et al., J. Biol. Chem. (1984) 259:8753–8757), imidazolinones (Shaner et al., Plant Physiol. (1984) 76:545–546), triazolopyrimidines (Subramanian et al., ACS Sym. Series 389 (1989) pp 277–288) and pyrimidyloxybenzoates (EPA 223 406, EPA 249 707 and EPA 249 708). Other classes of herbicides with ALS as the target include pyrimidylsalicylates, carbamoylpyrazolines, sulfonylimino-triazinyl heteroazoles, N-protected valylanilides, sulfonylamide azines, pyrimidyl madelie acids, benzenesulfonyl carboxamide compounds, substituted sulfonyldiamides, and ubiquinone-o. Transgenic plants with decreased sensitivity to inhibition by sulfonylurea and imidazolinone herbicides have been disclosed. Particular mention is made of EPA 0 525 384; U.S. Pat. Nos. 4,761,373; 5,198,599 and 5,331,107 and references cited therein.

Since many of the ALS inhibitor herbicides are known for their low mammalian toxicity, high herbicidal potency at low use rates and broad range crop selectivity, crop hybrids or varieties with resistance to these herbicides would provide an attractive solution to allowing herbicidal use without risk of damage to sensitive crops.

SUMMARY OF THE INVENTION

The present invention provides a novel functional acetolactate synthase enzyme (ALS) which exhibits resistance to herbicides which target ALS. The subject peptide isolated from a resistant cocklebur biotype was cloned and is described hereinafter. The invention also contemplates transgenic plants having enhanced resistance to herbicides which target ALS wherein a DNA sequence encoding the novel functional ALS resistant to herbicidal inhibition is introduced into a plant of interest. The plants can then be grown to produce seed having the resistant genotype.

It is to be understood that the following detailed description presents a single embodiment of the invention. This embodiment relates to a particular polypeptide and gene encoding the polypeptide which renders certain cocklebur plants tolerant or resistant to ALS inhibitor herbicides. However, it is understood that this gene may be made in whole or part by chemical or enzymatic synthetic methods.

BRIEF DESCRIPTION OF THE FIGURES

FIG. 1 shows the nucleic acid sequence of the resistant cocklebur biotype (SEQ ID No: 1). The amino acid translation product starts at nucleotide 111 corresponding to the beginning of the chloroplast targeting sequence. The mature protein starts at nucleotide 342.

FIG. 2 shows the amino acid sequence of the resistant cocklebur biotype (SEQ ID No: 2). Amino acid residues 1–77 depict the chloroplast targeting sequence and amino acid residues 78–648 depict the mature protein sequence.

FIG. 3 shows the nucleic acid sequence of wild type, sensitive cocklebur (SEQ ID No: 3).

FIG. 4 shows the amino acid sequence of wild type, sensitive cocklebur (SEQ ID No: 4).

DETAILED DESCRIPTION OF THE INVENTION

Figure 5:
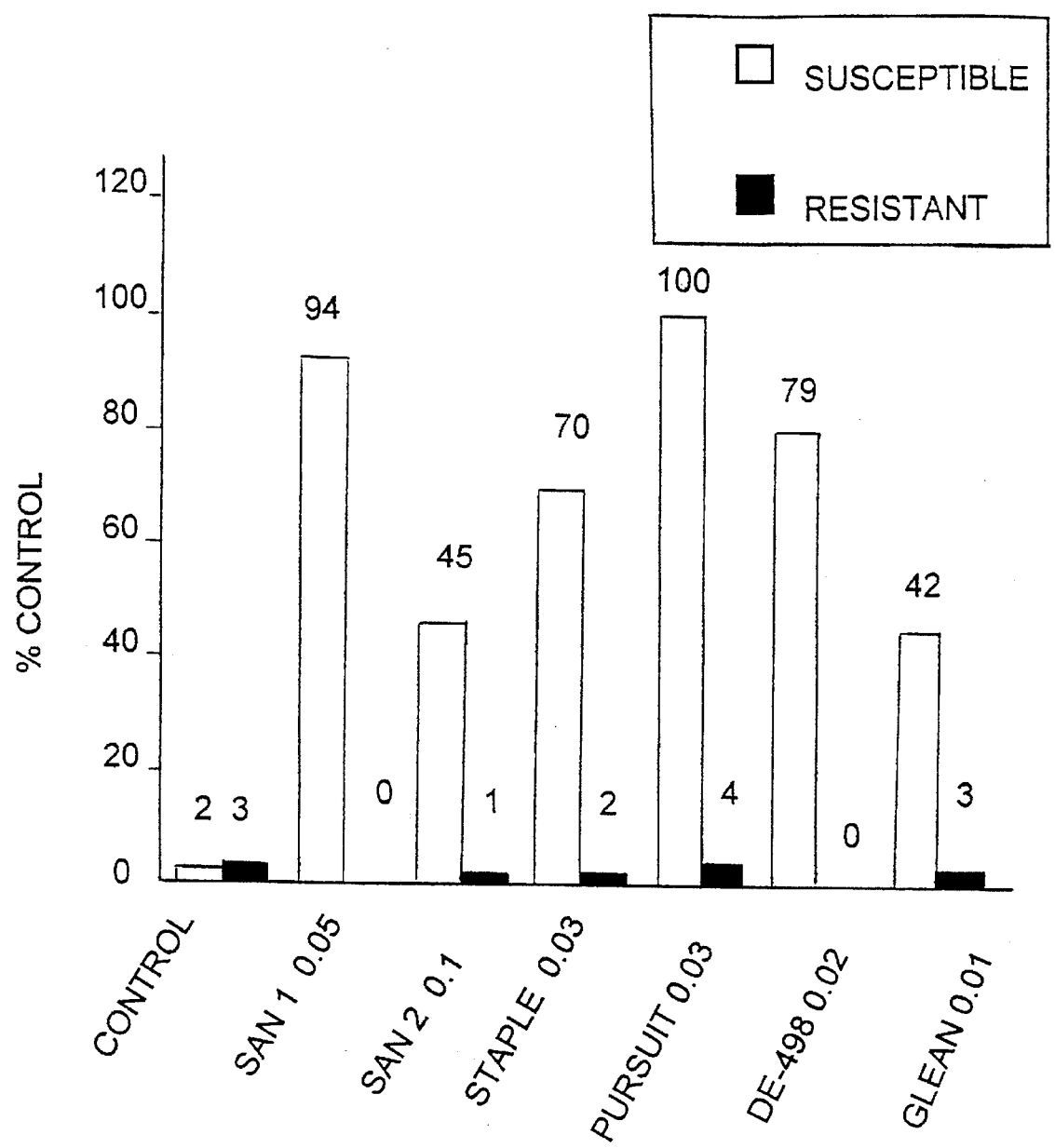
FIG. 5 depicts the comparison of ALS inhibitor herbicides against susceptible and resistant cocklebur.

The resistant cocklebur biotype (hereinafter R-XANST) was discovered in a soybean field characterized by a lack of crop rotation and the use of imidazolinone type herbicides.

The complete sequence of the R-XANST cDNA is described in FIG. 1 (SEQ ID No: 1) and the 2156 bp cDNA codes for a 648 residue protein described in FIG. 2 (SEQ ID No: 2). Also described is the 77 residue chloroplast targeting sequence. The cDNA sequence from wild type sensitive cocklebur (hereinafter S-XANST) is described in FIG. 3 (SEQ ID No: 3) and the corresponding protein is described in FIG. 4 (SEQ ID No: 4). The S-XANST is a 648 residue protein with a 77 residue chloroplast targeting sequence. The mature form (571 residues) is 89%, 86%, 78%, and 46% identical with respect to the amino acid residues to the corresponding enzyme from tobacco, arabidopsis, maize and yeast, respectively. The S-XANST and R-XANST sequences are 99.4% identical at the DNA level. Most of the mismatches occur on the third base of the codons and do not modify the translated product. It is well known in the art that the Proline and Serine/Alanine domains are important in conferring resistance to the ALS inhibitor. (See EP 0 525 384 and Lee, K. Y., et al., EMBO J. (1988) 7:1241–1248). In Lee et al. supra two distinct ALS genes were identified in tobacco. One resistant mutant was found to have a single Pro to Gln replacement at amino acid residue 196 and this gene was classified as a class I gene. In a second resistant mutant two amino acid changes were identified in the second ALS gene. This gene was classified as class II gene and included a replacement at amino acid residue 196, Proline to Alanine. A change at the amino acid residue 621 (Ala) is disclosed in EP 0 525 384. However, between the R-XANST and S-XANST of this invention there are no differences found in the Proline or Serine/Alanine domains.

With respect to the differences between S-XANST and R-XANST at the amino acid level there are five differences. These include the change of Lys (63) to Glu (63); Phe (258) to Leu (258); Gln (269) to His (269); Asn (522) to Ser (522) and Trp (552) to Leu (552). The change at residue 522 is the change of a basic residue to an uncharged residue. The changes at positions 522 and 552 are thought to be particularly important in conferring resistance or tolerance. Therefore this invention relates not only to a functional ALS enzyme having the amino acid sequence of SEQ ID No.: 2 but also to an enzyme having modifications to the amino acid sequence of SEQ ID No.:2 wherein said modifications include an amino acid sequence having the same function and about 90% or greater similarity to the sequence of SEQ ID No.:2 and more preferably having 95% or greater similarity. In this context similarity means having at least 90% identical or conservatively replaced amino acid residues in a like position. Additionally, modified functional ALS enzymes may have specific changes at amino acid residue 552 wherein said residue is other than Leu and is preferably but not limited to Ser, Arg, Gly and Cys.

ALS inhibitor compounds comprise a large class of structurally unrelated herbicidal compounds including sulfonylureas, imidazolinones, triazolopyrimidines, pyrimidyloxybenzoates and phthalides.

Representative examples of herbicidal sulfonylureas include:
chlorsulfuson, [2-chloro-N-[[CH-methoxy-6-methyl-1,3, 5-triazin-2-yl-amino]carbonyl]benzenesulfonamide];
metsulfuron, [2-[(L-4-methoxy-6-methyl-1,3,5-triazin-2-yl)amino]carbonyl];
thifensulfuron, {3-[[[[(4-methoxy-6-methyl-1,3,5-triazin-2-yl)amino]carbonyl]amino]sulfonyl]-2-thiophenecarboxylic acid};
bensulfuron, {2-[[[[[(4-6-dimethoxy-2-pyrimidinyl) amino]carbonyl]amino]sulfonyl]methyl]benzoic acid }; and
chlorimuron, {2-[[[[(4-chloro-6-methoxy-2-pyrimidinyl) amino]carbonyl]amino]sulfonyl]benzoic acid}.

Representative examples of herbicidal imidazolinones include:
imazapyr, {(+)-2-[4,5-dihydro-4-methyl-4-(1-methylethyl)-5-oxo-1H-imidazole-2-yl]-3-pyridinecarboxlyic acid};
imazaquin, {2-[4,5-dihydro-4-methyl-4-(1-methylethyl)-5-oxo-1H-imidazole-2-yl]-3-quinolinecarboxylic acid}; and
imazethapyr, {(+)-2-[4,5-dihydro-4-methyl-4-(1-methylethyl)-5-oxo-1H-imidazole-2-yl]-5-ethyl-3-pyridinecarboxylic acid}.

Certain phthalides exhibit general and selective herbicidal activity against plants. Members of this family include those compounds disclosed in EPA 461 079 and PCT WO/9110653 hereby incorporated by reference.

For the purpose of this specification the structurally different classes of herbicides referred to above which inhibit ALS as their primary site of action are collectively referred to as ALS inhibitor compounds or herbicides. The term herbicidally effective amount refers to the amount of herbicide which achieves inhibitive control or modification of undesired plant growth when applied to plants or to the area in which these plants are growing.

The term "herbicide resistance" as used herein concerning the R-XANST biotype means the naturally-occurring inheritable ability of a plant biotype within a plant population to survive a herbicide treatment that would, under normal conditions effectively control that population. Resistant is not due to the herbicidal dosage the resistant plant is able to withstand, but rather the difference in response between the response of the resistant biotype and the susceptible population. The term, when used in conjunction with genetic transformation or transgenic plants also means wherein resistance or tolerance is conferred by a foreign gene encoding an enzyme which is resistant to deactivation by an ALS herbicide or tolerant to a ALS herbicide at a concentration which would normally inhibit the activity of an unaltered enzyme. Resistance in this context includes resistance of a plant to multiple herbicides having the same target site due to the presence of a predominantly single resistance mechanism.

Recombinant DNA techniques may be used to obtain resistant lines of plants. These techniques include the use of nucleic acid sequences encoding the ALS derived from resistant plants. The ALS gene may be derived from cDNA or synthesized in whole or part. The advantage to synthesizing a gene is the desirability of modifying a portion of the codons to enhance expression by employing host preferred codons. Additionally DNA constructs of the invention may comprise not only the claimed nucleic acid sequences but also may include promoters, terminating sequences, polylinkers and other regulatory regions well known to those skilled in the art.

Promoters refer to nucleotide sequences at the 5'-end of a structural gene which direct the initiation of transcription and include all the regulatory regions required for transcription including the region coding for the leader sequence of mRNA. A number of promoters which are active in microbial and plant cells have been described in the literature. Suitable plant promoters include nopaline synthase (NOS), octopine synthase (OCS), cauliflower mosaic virus (CaMV) 19S and 35S, ribulose bisphosphate carboxylase (RUBISCO), and heat shock Brassica promoter (HSP 80). Suitable promoters used in the transformation of E. coli include, but are not limited to $P_{Tac}$, lambda $_{pr}$ and $T_7$ which are available commercially. The promoters used in the present invention may be modified to affect control characteristics and further may be a composite of segments derived from more than one source, naturally occurring or synthetic. Termination sequences refer to a nucleotide sequence at the end of a transcriptional unit that signals termination of transcription. Terminators are 3'-non-translated DNA sequences that contain a polyadenylated signal. Examples of terminators are known and described in the literature and include but are not limited to nos (nopaline synthase terminator), the 35S terminator of CaMV and the zein terminator.

Vectors comprising the nucleic acid sequences described above represent another embodiment of the invention. Expression vectors are typically plasmids. Plasmids in general are circular double stranded DNA loops including a promoter operably linked to the DNA sequence or sequences encoding the protein of interest, transcription termination sequences and the remaining vector with 3' and 5' elements. One skilled in the art is aware of many types of vectors including virus vectors, baculovirus; phage vectors; Agrobacterium-Ti plasmid; binary vectors and other vectors suitable for plant transformation. The insertion of the DNA sequences into plant host cells according to the invention occurs according to techniques known in the art.

Vectors of the invention may also include other DNA sequences known in the art, including but not limited to: a) stability sequences; b) one or more marker sequences, for example, antibiotic and other herbicide resistance markers including cat (chloramphenicol acetyl transferase), npt II (neomycin phosphotransferase II), PAT (phosphinothricin acetyltransferase the expression of which confers resistance to the herbicide Basta); EPSP (5-enolpyruvyl-shikimate 3-phosphate synthase, the enzyme inhibited by glyphosate, the active ingredient in the herbicide Roundup) and bxn (bromoxynil-specific nitrilase); c) signal sequences or leader peptides which are specific N-terminal sequences known to efficiently direct the mature peptide to the endoplasmic reticulum, vacuole or extracellular space via translocation through the endoplasmic reticulum membrane and which is excised during translocation; d) intron sequences; and e) enhancer or other elements necessary to increase or decrease levels of expression obtained in particular parts of plants under certain conditions. These examples are stated by way of example only and are not intended to limit the invention in any manner.

A wide variety of techniques are available and known in the art for carrying out plant cell or tissue transformation. These include but are not limited to, direct transfer of DNA into whole cells, tissues or protoplasts, optionally assisted by chemical or physical agents to increase cell permeability to DNA, for example treatment with polyethylene glycol, and dextran sulfate; electroporation, heat shock and ballistic implantation of DNA coated particles. Transformation is also mediated by Agrobactedum strains, notably *A. tumefaciens*, and also by various genetically engineered transformation plasmids which include portions of the T-DNA of the tumor inducing plasmids of Agrobactria. Other means for effecting entry of DNA into cells include the use of viral vectors, agroinfection, binary vectors and cotransformation. (See Jensen et al., (1993), Techniques for Gene Transfer, pp 125–146 in Transgenie Plants, vol. 1, eds. King and Wu, Academic Press). Transformed or transfected bacterial cells are included in the present invention, for example *E. coli* and *Bacillus thuringenis* (B.t.). Considerable experience in biotechnology has already been achieved and a wide variety of suitable operatively functional plasmids and transfer expression vectors systems are known and available for these organisms.

As used herein the term "genetic transformation" means the stable integration of a foreign gene into the genome of a plant regenerated from nucleic acid treated plant protoplasts, cells or tissue. "Transgenic plants" as used herein refers to plants carrying the stably integrated foreign gene. A "foreign gene" is a term used in the art to denote a gene or group of genes which has been transferred to a host cell or host plant from a source other than the host cell or host plant.

Virtually all plants of agronomic or horticultural value are known to be both transformable and regenerable, and all crop plants which may be sensitive to any herbicide of the ALS inhibitory herbicide class would be considered suitable host material. The techniques vary in individual detail from species to species as is well recognized by one skilled in the art. Means of regenerating plants are well documented in the literature. For a review on plant transformation and regeneration, see Ritchie and Hodges, pps. 147–178, in Kung and Wu, Transgenic Plants, vol. 1, 1993, Academic Press. Plant tissue includes differentiated and undifferentiated tissue and cells of plants including but not limited to roots, shoots, leaves, pollen, embryos, seed and various forms of aggregations of plant cells including callus.

Crop plants can be evaluated for ALS herbicide resistance to one or more herbicides of interest in the ALS inhibitor herbicide class, particularly a sulfonylurea, imidazolinone or phthalide by the ability of the plant to grow in the presence of the herbicide as compared to nontransgenic plants. Crop plants of particular interest include soybeans; cereal crops, such as maize; tomatoes; and sunflower. The invention herein provides not only for the transgenic plants, but also the seeds and progeny thereof which comprise and express the resistant R-XANST gene. In the field, genotypes expressing the R-XANST may be used with ALS inhibitory herbicides to effectively combat weed pests.

EXPERIMENTAL

Plant Material:

Cross-resistant seeds were obtained from Pemiscoll County Missouri (herein after R-XANST). The field from which the R-XANST seeds were obtained had been treated with imidazolinone herbicides during the 1990, 1991 and 1992 growing seasons. Susceptible cocklebur seeds were obtained from Azlin Seed Company (hereinafter S-XANST).

Herbicidal Evaluations:

Seeds of S-XANST and R-XANST are planted one per pot in soil mix. Pots are placed on a heating mat and the soil temperature increased from about 65° F. to about 90° F. At the 2–3 leaf stage, plants are treated with test herbicides using a linear track laboratory sprayer calibrated to deliver 42.5 GPA. Plants are watered by subirrigation after herbicide application. Observations of percent control are made 21 days after herbicide application. The test ALS inhibitor herbicides are listed below including their chemical class:

Broadstrike, common name: flumetsulam also known as DE-498, (triazolopyrimidine sulfonanilide) applied at 0.02 lb ai/A;

Glean, common name: chlorsulfuron, (sulfonyl-urea) applied at 0.01 lb ai/A;

Staple, common name: pyrthiobac-sodium, (benzoate phthalide) applied at 0.03 lb ai/A;

3-[(4,6-Dimethoxy-2-pyrimidinyl)carbonyl]-N,N-dimethyl-2-pyridinecarboxamide, (phthalide) hereinafter SAN 1, applied at 0.05 lb ai/A;

3-6-Dichloro-2-[(4,6-dimethoxy-2-pyrimidinyl)carbonyl] benzoic acid, isopropyl ammonium salt, (phthalide), hereinafter SAN 2, applied at 0.1 lb ai/A and Pursuit, common name: imazethapyr (imidazolinone) applied at 0.03 lb ai/A.

The effect of the various ALS inhibitors against R-XANST and S-XANST is depicted in FIG. 5. The results are reported as % control wherein 100% injury is equal to complete control as determined by growth. All treatments are replicated four times in a randomized complete block design. This data confirms the presence of resistance of XANST to different classes of herbicides, which had previously been unknown, particularly resistance was unknown to the phthalide herbicidal compounds.

Additionally tests are preformed at much higher herbicide rates to determine the extent of resistance. SAN 2 performed greater than 95% injury to S-XANST at 0.1 lb ai/A. However, even at 30 lb ai/A the injury to R-XANST did not exceed 50% injury. At 0.03 lb ai/A Staple provides greater than 90% injury to S-XANST, but injury to R-XANST did not exceed 55% at the highest test rate, 9.0 lb ai/A. Broadstrike at 0.01 lb ai/A causes greater than 95% injury to S-XANST, but application of 6 lb ai/A produced only 25 % injury on R-XANST. Glean tested at 1.56 lb ai/A, a rate of 100 times field use, provided 88% injury to R-XANST. Pursuit provides 90% injury to R-XANST when used at 100 times the normal field rate, (6.25 lb ai/A).

Enzymatic evaluations:

Cocklebur is grown in a greenhouse. Five grams of fresh green leaf tissue are ground to a powder in a mortar at the temperature of liquid nitrogen. The powder is extracted with 100 ml of buffer containing 50 mM N-[2-hydroxyethyl] piperazine-N'-[3-propanesulfonic acid], (EPPS); pH 7.2; 5 mM $MgCl_2$; 2 mM EDTA; 1 mM valine; 1 mM leucine; 10% glycerol; 10 mM pyruvate; 5 mM Dithiothreitol; 1% polyvinyl polypyrrolidone (PVPP) and 10 µdM flavin adenine dinucleotide and filtered through cheesecloth. The filtrate was centrifuged at 15,000×g for 15 min.

The procedures used for the isolation of ALS from cocklebur are similar to those known in the art. The supernatant resulting from centrifugation of the crude extract is brought to 40% ammonium sulfate. The ammonium sulfate pellet is not frozen and is resuspended in standard buffer used for $I_{50}$ determinations and then gel-filtered through the same buffer. This preparation is used for determinations of Km for pyruvate and $I_{50}$. The Km is equal to the substrate concentration at which the initial reaction velocity is half maximal and also referred to as the Michaelis-Menten constant. The Km is determined using Lineweaver-Burke double reciporcial plots. $I_{50}$ is the concentration in which 50% inhibition is observed and is determined from linear regression analysis of the linear portion of the dose/response curve.

Substrate saturation with pyruvate is hyperbolic for R-XANST and S-XANST The Km value for R-XANST is 6 mM and is very close to the Km value of the S-XANST enzyme which is 3 mM. This result suggests that the resistant enzyme is unimpaired with respect to pyruvate.

The $I_{50}$ values by various ALS inhibitors are determined on both sensitive enzymes isolated from S-XANST and resistant enzymes isolated from R-XANST and are reported in Table 1. The results indicate that the resistant enzyme is highly resistant to the ALS inhibitors tested.

TABLE 1

| COMPOUND | $I_{50}$ (M) Sensitive | $I_{50}$ (M) Resistant | Fold-resistance (R/S) |
|---|---|---|---|
| Chlorsulfurson | $8 \times 10^{-9}$ | $5 \times 10^{-5}$ | 6,250 |
| Broadstrike | $6 \times 10^{-8}$ | $6 \times 10^{-4}$ | 10,000 |
| Imazaquin | $4 \times 10^{-7}$ | $1 \times 10^{-4}$ | 250 |
| Imazethapyr | $1 \times 10^{-6}$ | $1 \times 10^{-4}$ | 100 |
| Di-Cl benzoate | $9 \times 10^{-8}$ | $6 \times 10^{-4}$ | 2,200 |

TABLE 1-continued

| COMPOUND | $I_{50}$ (M) Sensitive | $I_{50}$ (M) Resistant | Fold-resistance (R/S) |
|---|---|---|---|
| Picolinate | $9 \times 10^{-8}$ | $1 \times 10^{-3}$ | 1,100 |
| Leucine | $1 \times 10^{-3}$ | $1 \times 10^{-3}$ | 1 | cDNA sequencing:

1. Preparation of polyA+mRNA from S-XANST and R-XANST.

Mature green leaves are obtained from S-XANST plants at the flowering stage. The guanidium isothiocyanate method is used for preparation of total RNA from leaves. (See Chirgwin, J. J. et al., (1979) Biochemistry 18:5294). The total RNA is further purified by standard CsCl gradient preparation and ethanol precipitation. (See Ausubel, F. M. et al., (1993) Current Protocols in Molecular Biology, Wiley & Sons Publishers, New York). RNA quality is checked by the presence on a formaldehyde gel of the two undegraded rRNA bands according to procedures standard in the art. The mRNA fraction is isolated from the total RNA by affinity chromatography on oligo (dT) cellulose using the procedure described in Aviv, H. and Leder, P., (1972), Purification of biologically active globin messenger RNA by chromatography on oligothymidylic acid-cellulose., Proc. Natl. Acad. Sci. 69:1408–1412. The mRNA fraction represents about 1% of the total RNA.

2. Preparation of double stranded cDNA.

Double stranded cDNA is synthesized using the Pharmacia-LKB (Piskataway, N.J.) cDNA synthesis kit using 10 µg of poly A+mRNA and oligo d(T) primers (Pharmacia-LKB). Using the same kit, NoII/EcoRI linkers/ adaptors are added and the constructs purified by gel chromatography on Sephacryl-S-400 (Pharmacia-LKB).

3. Construction of a cDNA library from S-XANST.

The cDNA from S-XANST is cloned by ligation into EcoRI digested and dephosphorylated λgt10 arms (Promega Corp., Madison Md.). The ligation mixture is packaged into phage extracts (Promega) and used to infect c600 Hfl *E. Coli*. The phage library obtained has a complexity of $10^5$ different phages, large enough to obtain several copies of the ALS cDNA.

4. Design of degenerated PCR primers for the amplification of a partial ALS gene from any organism, to be used as a screening probe.

ALS sequences from different organisms are obtained from GeneBank. They are used to define two evolutionary conserved regions for PCR primer design. From alignment of the known sequences of maize, tobacco, Brassica, arabidopsis and yeast, degenerated primers designated ALS-1 and ALS-2 are obtained from Keystone Laboratories, Inc. (Menlo Park, Calif.).

The ALS-1 primer corresponds to the amino acid sequence Met Leu Gly Met His Gly, (SEQ ID No: 5) and the nucleotide sequence ATG[CT]T[ACTG]GG[ACTG] ATGCA[CT]GG (SEQ. ID No: 6).

The ALS-2 complement primer corresponds to the amino acid sequence Val Gly Gln His Gln Met Trp/Phe (SEQ ID No: 7) and the nucleotide sequence GT[ACGT]GG[CAGT] CA[AG]CA[CT]CA[AG]ATGT (SEQ ID No: 8), and the real primer corresponds to the sequence ACAT[CT]TG[AG] TG[CT]TG[ACTG]CC[ACGT]AC (SEQ ID No: 9).

5. PCR amplification, cloning and sequencing of a fragment of S-XANST.

Using 10 ng of S-XANST cDNA obtained in step 2, and the primers designed in step 4, a 400 bp cDNA fragment is amplified, and cloned into the sequencing vector pBluescript (Stratagene, LA Jolla Calif.) to yield the plasmid pSCI696.

the extend of the different sequences obtained. The sequence is disclosed for the primers hereinbelow.

| T3, | ATTAACCCTCACTAAAG | (SEQ ID No: 13); |
|---|---|---|
| T7, | AAATACGACTCACTATAG | (SEQ ID No: 14); |
| CALSNC, | CGGAGGAATAGCTTCGCC | (SEQ ID No: 15); |
| CALSC, | GGCGAAGCTATTCCTCCG | (SEQ ID No: 16); |
| 671A, | CGGTTTGTGGAGCTTACGGGG | (SEQ ID No: 17); |
| 672A, | GCAGCTATTCAGAGAATGTTGG | (SEO ID No: 18); |
| 672B, | CAATATTCATTCTGCCGTCG | (SEQ ID No: 19); |
| 672C, | CTTCATAACCGACAAACTGC | (SEQ ID No: 20); |
| 673A, | GTCTGTATTGCAACCTCTGG | (SEQ ID No: 21); |
| 673B, | CAATCCTGGGAATATCC | (SEQ ID No: 22); |
| 673C, | GTAGCTCCAGGACCAGAGG | (SEQ ID No: 23); |
| CK_ALS_1, | CATTCAACAATGGCGGCCATCC | (SEQ ID No: 24); |
| CK_ALS_2, | GCATAATTCGCATAAACGGTCCC | (SEQ ID No: 25); and |
| CK_ALS_3 | CAGCAAACTTCAACATGTTAGGG | (SEQ ID No: 26). |

The plasmid is completely sequenced using the standard dedeoxy termination method and [$^{33}$P]dATP labeling. The sequencing products are separated on saturated urea polyacrylamide gel electrophoresis, fixed and exposed for autoradiography. These methods are standard methods known to those skilled in the art and described in Ausubel, F. M. et al., (1993) Current Protocols in Molecular Biology, Wiley & Sons, New York. The 100 amino acid residue sequence shows 75 % amino acid residue identity with Arabidopsis ALS.

6. Screening of the library for S-XANST.

The library obtained above in step 3 is screened with a $^{32}$P-labelled probe obtained by random labelling of the PCR fragment obtained in step 4. Three rounds of screening provided successive enrichment of positive plaques from 8 in $10^5$ to 6 in 1000 to 4 in 4. DNA from these four positives is prepared using the Promega kit (Magic DNA lambda prep). The size of the cDNA insert for each is determined by PCR using the primers gt10L and gt10R that anneal on the lambda vector around the cloning site.

The gt10L primer has a nucleotide sequence corresponding to

GTTCAGCCTGGTTAAGTCCAAGC (SEQ ID No: 10).

The gt10R primer has a nucleotide sequence corresponding to GAGTATTCTTTCCAGGGTAAAAAGC (SEQ ID No: 11).

The sizes correspond to 2.5 kb, 2.4 kb, 1.6 kb and 1.1 kb. Using the ALS specific PCR primer CALSC; GGCGAAGC-TATTCCTCCG (SEQ ID No: 12) and gt10R, it is determined that the 5' untranslated region (between the stop codon and the polyadenylation site ) is about 460 bp for all cDNAs. The largest one therefore has a coding region about 2 kb allowing the encoding of 660 amino acids.

7. Sequencing the S-XANST clones.

Figure 6:
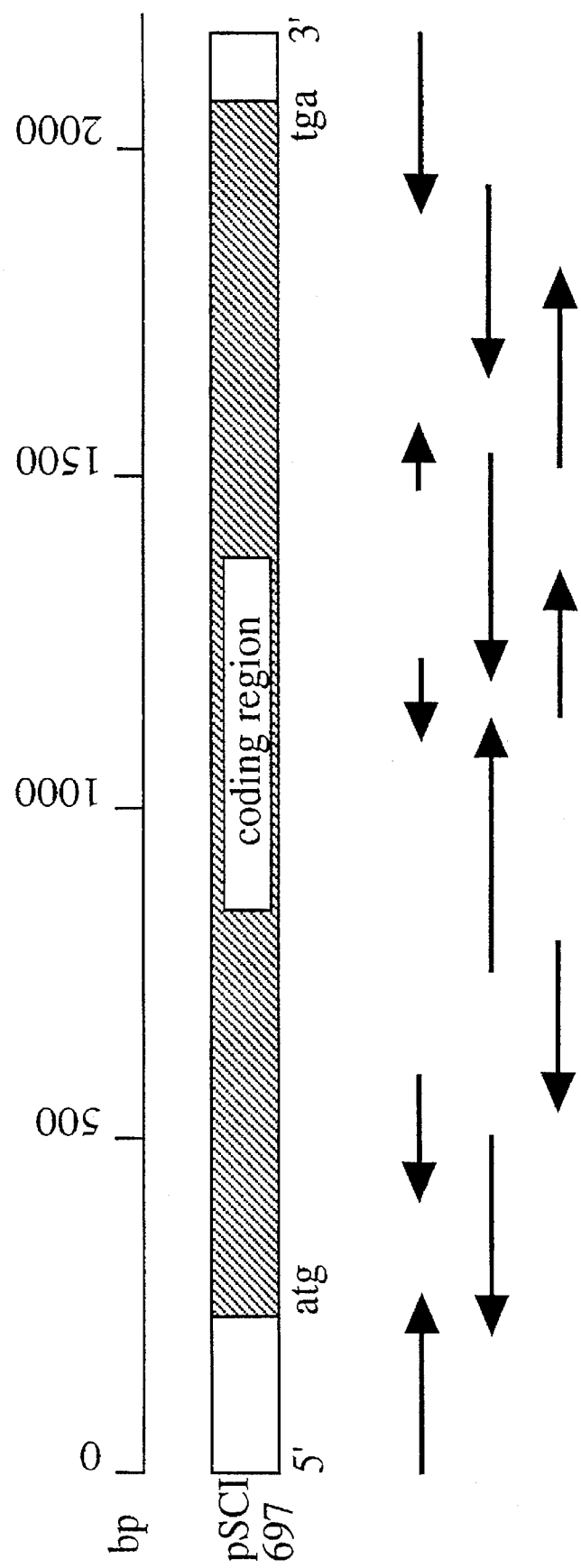
FIG. 6 depicts the map of pSCI 697 and the relative position of subclones.
Figure 7:
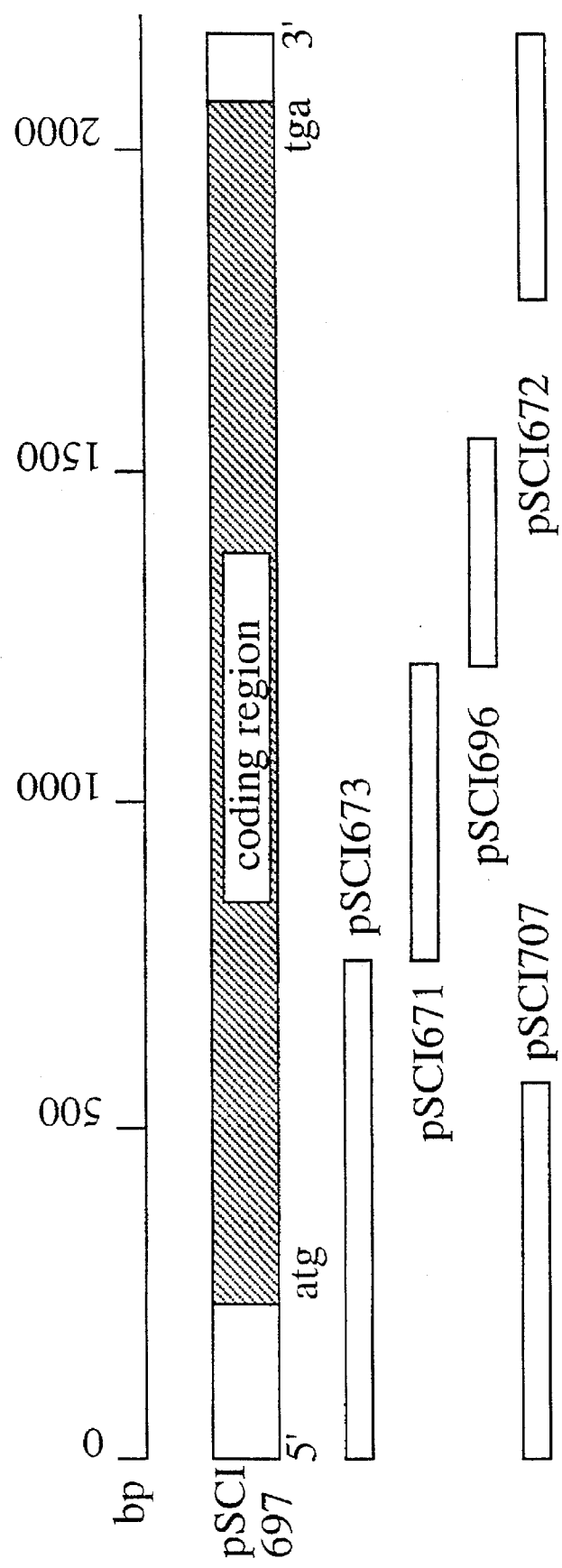
FIG. 7 depicts the sequencing strategy for susceptible cocklebur clones.

The cDNA from the largest clone from the four positives is used, and is amplified using gt10L and gt10R. The resulting fragment is cloned into pBluescript (Stratagene), generating the plasmid pSCI697. FIG. 6 gives the map of pSCI697, and the relative position of the subclones generated by restriction digest. HindIII digest of pSCI697 and subsequent cloning of the HindIII pieces into new pBluescript give the plasmids pSCI671, pSCI672 and pSCI673. Another subclone is obtained by PCR amplification of the lambda DNA using gt10L and 673C (pSCI707). The plasmids are sequenced using the primers T3, T7 (Stratagene), specific for the polylinker of pBluescript, and the primers designated, CALSNC, CALSC, 671A, 672A, 672B, 672C, 673A, 673B, 673C, CK_ALS_1, CK_ALS_2, and CK_ALS_3, specific for the ALS sequence. FIG. 7 depicts FIG. 3 (SEQ ID No: 3) gives the complete nucleotide sequence of pSCI697 with the translation of the coding region. S-XANST is a 648 residue protein as described in FIG. 4 (SEQ ID No: 4) with a 77 residue chloroplast targeting sequence.

8. Sequencing of R-XANST.

Figure 8:
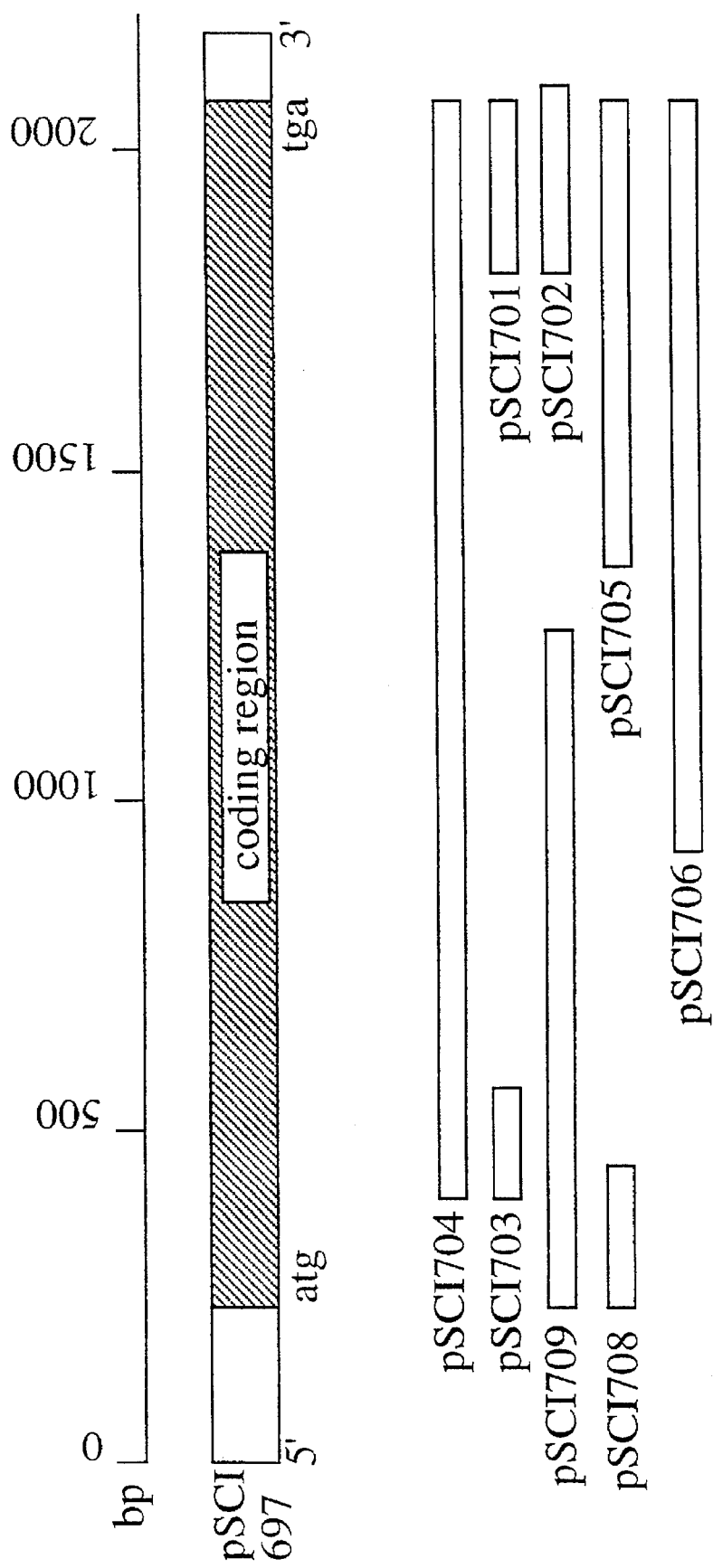
FIG. 8 depicts the relative position of the subclones for resistant cocklebur.

Double stranded cDNA is prepared as above from mature leaves of the R-XANST. 10 ng of the double stranded DNA is used in the PCR amplification of the ALS. This is achieved in two fragments. The first fragment is amplified with the primer 673A and 672B and cloned into pBluescript as above to generate pSCI704. The second fragment is amplified with CK_ALS_1 and CK_ALS_3 and cloned into pSCI709. Partial clones are also obtained and cloned using CK_ALS_1 and 673C (pSCI708), 671A and 672B (pSCI706), CALSC and 672B (pSCI705), 672A and 672C (pSCI702), 672A and 672B (pSCI701), 673A and 673B (pSCI703). The relative position of these clones with respect to pSCI697 is given in FIG. 8. The sequence of these clones is established using the primers described hereinabove. FIG. 1 (SEQ ID No: 1) gives the complete nucleotide sequence of the cDNA of R-XANST with the translation of the coding region. The S-XANST and R-XANST are 99.4% identical at the DNA level. R-XANST is a 648 residue protein as described in FIG. 2 (SEQ ID No: 2) with a 77 residue chloroplast targeting sequence. The use of these primers is also one aspect of the instant invention.

What is claimed is:

1. An isolated nucleic acid sequence encoding a functional acetolactate synthase enzyme (ALS) having an amino acid sequence of SEQ ID No: 2 or a modified ALS thereof wherein said modified ALS has about 90% or greater amino acid sequence similarity with the amino acid sequence of SEQ ID No.: 2 said ALS or modified ALS exhibiting herbicidal resistance to ALS herbicides.

2. A nucleic acid sequence according to claim 1 wherein said ALS herbicide is selected from the group consisting of herbicidally effective sulfonylureas, imidazolinones, triazolopyrimidines, pyrimidyloxybenzoates and phthalide compounds.

3. A nucleic acid sequence according to claim 1 wherein said ALS herbicide is a herbicidally effective phthalide compound.

4. A nucleic acid sequence according to claim 1 wherein said ALS herbicide is a herbicidally effective sulfonylurea herbicide and a herbicidally effective phthalide compound.

5. A nucleic acid sequence according to claim 1 wherein said ALS exhibits herbicidal resistance to herbicidally effective imidazolinone herbicides and to herbicidally effective phthalide compounds.

6. A nucleic acid sequence according to claim 1 wherein the sequence encodes an amino acid sequence from residue 78 to residue 648.

7. A transformation vector comprising the nucleic acid sequence of claim 1.

8. A host cell comprising the nucleic acid sequence of claim 1.

9. A nucleic acid construct comprising the sequence of claim 1 operably linked to a promoter that functions in plants.

10. A method of conferring ALS herbicide resistance to a plant which comprises providing a plant cell with the nucleic acid sequence of claim 1.

11. A method of conferring phthalide specific ALS herbicide resistance to a plant cell comprising incorporating into the genome of the plant cell through known plant transformation methods the nucleic acid sequence of claim 1.

12. The isolated nucleic acid sequence of SEQ ID No:1 encoding a functional ALS tolerant to inhibition by ALS herbicides.

13. The sequence according to claim 12 wherein the ALS herbicide is a herbicidally effective amount of a phthalide compound.

14. A plant wherein the growth and development of said plant is resistant to ALS inhibition by an ALS herbicide at levels which normally inhibit the growth and development of said plant wherein said resistance is conferred by the introduction of a nucleic acid sequence according to claim 1.

15. A plant wherein the growth and development of said plant is resistant to ALS inhibition by an ALS herbicide at levels which normally inhibit the growth and development of said plant wherein said resistance is conferred by a heterologous ALS with an amino acid sequence as described in SEQ ID No:2 or a modified ALS thereof wherein said modified ALS has about 90% or greater amino acid sequence similarity with the amino acid sequence of SEQ ID No.:2.

16. A plant according to claim 14 wherein said plant is maize.

17. A plant according to claim 14 wherein said ALS herbicide is selected from the group consisting of sulfonylureas, imidazolinones and phthalides.

18. An isolated nucleic acid sequence according to claim 1 wherein the encoded amino acid residue at position 552 is other than leu.

* * * * *

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 2156 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
GAACAACAGC CACATGTTTC TGGACCATCG TCGTTCACAC CTATTTAAT CAGATAAACA      60
AAGTACAAAC ATAACATAAC ATAACCCTAG TACATAACAC ACATTCAACA ATGGCGGCCA    120
TCCCTCATAC AAACCCTTCC ATCACCACCA AACCACCCTC ATCTCCACCA CGTCCCACCT    180
TCCTCGCCCG TTTCACATTC CCAATAACCT CCACTTCCCA TAAACGACAC CGTCTCCACA    240
TCTCCAACGT CCTCTCCGAC TCCAAACCCA CCATCACCCA TTCACCATTA CCAACCGAAT    300
CATTTATCTC CCGTTACGCT CCAGACCAAC CAAGAAAAGG CGCTGATGTT CTCGTCGAAG    360
CTCTGGAACG TGAAGGCGTT ACAGACGTCT TCGCTTACCC AGGTGGTGCC TCCATGGAGA    420
TCCACCAAGC TCTCACGCGC TCAACCACCA TCCGCAACGT TCTCCCACGT CACGAACAGG    480
GCGGCGTCTT TGCTGCCGAA GGCTACGCAC GTGCCTCCGG TCTTCCCGGC GTCTGTATTG    540
CAACCTCTGG TCCTGGAGCT ACGAACCTAG TAAGTGGTCT TGCTGATGCT TTATTAGACA    600
GTGTTCCAAT GGTTGCTATT ACTGGTCAAG TTCCCAGGAG AATGATTGGA ACAGATGCGT    660
TTCAAGAAAC CCCTATTGTT GAGGTAACAC GTTCCATTAC TAAGCATAAT TATTTAGTTT    720
TGGATGTCGA GGATATTCCC AGGATTGTTA GGGAAGCTTT TTATCTTGCG TCTTCTGGTC    780
GACCCGGACC GGTTTTAATT GATGTACCTA AGGATATACA GCAGCAGTTG GTAGTGCCTA    840
AATGGGATGA GCCTATTAGG TTACCTGGGT ATTTGTCTAG GTTGCCTAAA ACGGAGAATA    900
ATGGGCAGTT GGAACACATT GTTAGGTTGG TGAGTGAGGC CAAGAGGCCG GTTTTGTATG    960
TGGGGGGTGG GTGTTTGAAT TCGGGAGATG AGTTGAGGCG GTTTGTGGAG CTTACGGGGA   1020
TACCGGTTGC GAGTACGTTG ATGGGCTTG GAGCGTACCC TGCTTCTAGT GATTTGTCGC   1080
TGCATATGCT TGGGATGCAT GGGACGGTTT ATGCGAATTA TGCGGTTGAT AAGAGTGATT   1140
TGTTGCTTGC GTTTGGGGTA AGGTTTGATG ACCGTGTGAC GGGGAAGCTT GAGGCTTTTG   1200
CTAGCAGAGC TAAGATTGTT CATATTGATA TTGATTCTGC GGAAATTGGG AAGAATAAGC   1260
AGCCTCATGT GTCGATTTGT GGTGATATCA AGGTCGCGTT ACAGGGTCTG AACAAGATTT   1320
TGGAGGTAAA GAATTCGGTG ACTAATCTTG ATTTCTCGAA CTGGAGGAAG GAATTGGATG   1380
AGCAAAAGGT TAAGTATCCG TTGAGTTTTA AAACATTTGG CGAAGCTATT CCTCCGCAGT   1440
ATGCCATTCA AGTGCTTGAT GAGTTAACGG GTGGGAATGC GATTATTAGC ACTGGGGTCG   1500
GGCAGCATCA GATGTGGGCT GCTCAGTTTT ACAAATACAA CAAGCCTAGA CAATGGCTGA   1560
CGTCAGGTGG ACTAGGCGCG ATGGGTTTTG GGTTGCCCGC TGCTATCGGG GCGGCTGTTG   1620
CAAGACCTGA TGCGGTAGTA GTTGATATCG ATGGTGATGG AAGCTTTATA ATGAGCGTTC   1680
AAGAGTTAGC CACAATCCGT GTTGAAAATC TTCCTGTTAA GATTTTGTTA CTTAACAATC   1740
AGCATTTGGG TATGGTGGTT CAGTTGGAGG ATCGGTTTTA CAAGGCGAAT CGGGCTCATA   1800
```

| CCTACTTAGG | AAATCCGTCA | AAAGAGTCTG | AAATATTCCC | TAACATGTTG | AAGTTTGCTG | 1860 |
| AAGCGTGTGA | TATCCCAGCT | GCCCGAGTGA | CCCGGAAGGC | AGATCTACGA | GCAGCTATTC | 1920 |
| AGAAGATGTT | GGATACACCG | GGGCCTTACT | TGTTGGATGT | GATCGTGCCC | CATCAAGAAC | 1980 |
| ATGTGTTGCC | CATGATCCCG | GCTGGTGGAG | GTTTCATGGA | TGTGATCACC | GAAGGCGACG | 2040 |
| GCAGAATGAA | ATATTGAGCT | TCAATGTCAC | ATATAGTGTG | TTCTGTAAGC | AGTTTGTCGG | 2100 |
| TTATGAAGTT | AAATGTTTTG | TTGTGTAATT | TCGTTCCTGG | TTAAAAAATC | AAGCTT | 2156 |

( 2 ) INFORMATION FOR SEQ ID NO:2:

( i ) SEQUENCE CHARACTERISTICS:
        ( A ) LENGTH: 648 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:2:

```
Met Ala Ala Ile Pro His Thr Asn Pro Ser Ile Thr Thr Lys Pro Pro
 1               5                  10                  15

Ser Ser Pro Pro Arg Pro Thr Phe Leu Ala Arg Phe Thr Phe Pro Ile
                20                  25                  30

Thr Ser Thr Ser His Lys Arg His Arg Leu His Ile Ser Asn Val Leu
            35                  40                  45

Ser Asp Ser Lys Pro Thr Ile Thr His Ser Pro Leu Pro Thr Glu Ser
        50                  55                  60

Phe Ile Ser Arg Tyr Ala Pro Asp Gln Pro Arg Lys Gly Ala Asp Val
65                  70                  75                  80

Leu Val Glu Ala Leu Glu Arg Glu Gly Val Thr Asp Val Phe Ala Tyr
                85                  90                  95

Pro Gly Gly Ala Ser Met Glu Ile His Gln Ala Leu Thr Arg Ser Thr
            100                 105                 110

Thr Ile Arg Asn Val Leu Pro Arg His Glu Gln Gly Gly Val Phe Ala
        115                 120                 125

Ala Glu Gly Tyr Ala Arg Ala Ser Gly Leu Pro Gly Val Cys Ile Ala
    130                 135                 140

Thr Ser Gly Pro Gly Ala Thr Asn Leu Val Ser Gly Leu Ala Asp Ala
145                 150                 155                 160

Leu Leu Asp Ser Val Pro Met Val Ala Ile Thr Gly Gln Val Pro Arg
                165                 170                 175

Arg Met Ile Gly Thr Asp Ala Phe Gln Glu Thr Pro Ile Val Glu Val
            180                 185                 190

Thr Arg Ser Ile Thr Lys His Asn Tyr Leu Val Leu Asp Val Glu Asp
        195                 200                 205

Ile Pro Arg Ile Val Arg Glu Ala Phe Tyr Leu Ala Ser Ser Gly Arg
    210                 215                 220

Pro Gly Pro Val Leu Ile Asp Val Pro Lys Asp Ile Gln Gln Gln Leu
225                 230                 235                 240

Val Val Pro Lys Trp Asp Glu Pro Ile Arg Leu Pro Gly Tyr Leu Ser
                245                 250                 255

Arg Leu Pro Lys Thr Glu Asn Asn Gly Gln Leu Glu His Ile Val Arg
            260                 265                 270

Leu Val Ser Glu Ala Lys Arg Pro Val Leu Tyr Val Gly Gly Gly Cys
        275                 280                 285

Leu Asn Ser Gly Asp Glu Leu Arg Arg Phe Val Glu Leu Thr Gly Ile
```

|     |     |     |     |     | 290 |     |     |     | 295 |     |     |     | 300 |     |
| --- | --- | --- | --- | --- | --- | --- | --- | --- | --- | --- | --- | --- | --- | --- |
| Pro | Val | Ala | Ser | Thr | Leu | Met | Gly | Leu | Gly | Ala | Tyr | Pro | Ala | Ser | Ser |
| 305 |     |     |     |     | 310 |     |     |     | 315 |     |     |     |     | 320 |
| Asp | Leu | Ser | Leu | His | Met | Leu | Gly | Met | His | Gly | Thr | Val | Tyr | Ala | Asn |
|     |     |     |     | 325 |     |     |     |     | 330 |     |     |     |     | 335 |
| Tyr | Ala | Val | Asp | Lys | Ser | Asp | Leu | Leu | Leu | Ala | Phe | Gly | Val | Arg | Phe |
|     |     |     | 340 |     |     |     |     | 345 |     |     |     |     | 350 |     |
| Asp | Asp | Arg | Val | Thr | Gly | Lys | Leu | Glu | Ala | Phe | Ala | Ser | Arg | Ala | Lys |
|     |     | 355 |     |     |     |     |     | 360 |     |     |     | 365 |     |     |
| Ile | Val | His | Ile | Asp | Ile | Asp | Ser | Ala | Glu | Ile | Gly | Lys | Asn | Lys | Gln |
|     | 370 |     |     |     |     | 375 |     |     |     |     | 380 |     |     |     |
| Pro | His | Val | Ser | Ile | Cys | Gly | Asp | Ile | Lys | Val | Ala | Leu | Gln | Gly | Leu |
| 385 |     |     |     |     | 390 |     |     |     |     | 395 |     |     |     |     | 400 |
| Asn | Lys | Ile | Leu | Glu | Val | Lys | Asn | Ser | Val | Thr | Asn | Leu | Asp | Phe | Ser |
|     |     |     |     | 405 |     |     |     |     | 410 |     |     |     |     | 415 |     |
| Asn | Trp | Arg | Lys | Glu | Leu | Asp | Glu | Gln | Lys | Val | Lys | Tyr | Pro | Leu | Ser |
|     |     |     | 420 |     |     |     |     | 425 |     |     |     |     | 430 |     |
| Phe | Lys | Thr | Phe | Gly | Glu | Ala | Ile | Pro | Pro | Gln | Tyr | Ala | Ile | Gln | Val |
|     |     | 435 |     |     |     |     | 440 |     |     |     |     | 445 |     |     |
| Leu | Asp | Glu | Leu | Thr | Gly | Gly | Asn | Ala | Ile | Ile | Ser | Thr | Gly | Val | Gly |
|     | 450 |     |     |     |     | 455 |     |     |     |     | 460 |     |     |     |
| Gln | His | Gln | Met | Trp | Ala | Ala | Gln | Phe | Tyr | Lys | Tyr | Asn | Lys | Pro | Arg |
| 465 |     |     |     |     | 470 |     |     |     |     | 475 |     |     |     |     | 480 |
| Gln | Trp | Leu | Thr | Ser | Gly | Gly | Leu | Gly | Ala | Met | Gly | Phe | Gly | Leu | Pro |
|     |     |     |     | 485 |     |     |     |     | 490 |     |     |     |     | 495 |     |
| Ala | Ala | Ile | Gly | Ala | Ala | Val | Ala | Arg | Pro | Asp | Ala | Val | Val | Val | Asp |
|     |     |     | 500 |     |     |     |     | 505 |     |     |     |     | 510 |     |
| Ile | Asp | Gly | Asp | Gly | Ser | Phe | Ile | Met | Ser | Val | Gln | Glu | Leu | Ala | Thr |
|     |     | 515 |     |     |     |     | 520 |     |     |     |     | 525 |     |     |
| Ile | Arg | Val | Glu | Asn | Leu | Pro | Val | Lys | Ile | Leu | Leu | Leu | Asn | Asn | Gln |
|     | 530 |     |     |     |     | 535 |     |     |     |     | 540 |     |     |     |
| His | Leu | Gly | Met | Val | Val | Gln | Leu | Glu | Asp | Arg | Phe | Tyr | Lys | Ala | Asn |
| 545 |     |     |     |     | 550 |     |     |     |     | 555 |     |     |     |     | 560 |
| Arg | Ala | His | Thr | Tyr | Leu | Gly | Asn | Pro | Ser | Lys | Glu | Ser | Glu | Ile | Phe |
|     |     |     |     | 565 |     |     |     |     | 570 |     |     |     |     | 575 |     |
| Pro | Asn | Met | Leu | Lys | Phe | Ala | Glu | Ala | Cys | Asp | Ile | Pro | Ala | Ala | Arg |
|     |     |     | 580 |     |     |     |     | 585 |     |     |     |     | 590 |     |
| Val | Thr | Arg | Lys | Ala | Asp | Leu | Arg | Ala | Ala | Ile | Gln | Lys | Met | Leu | Asp |
|     |     | 595 |     |     |     |     | 600 |     |     |     |     | 605 |     |     |
| Thr | Pro | Gly | Pro | Tyr | Leu | Leu | Asp | Val | Ile | Val | Pro | His | Gln | Glu | His |
|     | 610 |     |     |     |     | 615 |     |     |     |     | 620 |     |     |     |
| Val | Leu | Pro | Met | Ile | Pro | Ala | Gly | Gly | Gly | Phe | Met | Asp | Val | Ile | Thr |
| 625 |     |     |     |     | 630 |     |     |     |     | 635 |     |     |     |     | 640 |
| Glu | Gly | Asp | Gly | Arg | Met | Lys | Tyr |     |     |     |     |     |     |     |     |
|     |     |     |     | 645 |     |     |     |     |     |     |     |     |     |     |     |

(2) INFORMATION FOR SEQ ID NO:3:

(i) SEQUENCE CHARACTERISTICS:
        (A) LENGTH: 2156 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:3:

| | | | | | | |
|---|---|---|---|---|---|---|
| GAACAACAGC | CACATGTTTC | TGGACCATCG | TCGTTCACAC | CTATTTTAAT | CAGATAAACA | 60 |
| AAGTACAAAC | ATAACATAAC | ATAACCCTAG | TACATAACAC | ACATTCAACA | ATGGCGGCCA | 120 |
| TCCCTCATAC | AAACCCTTCC | ATCACCACCA | AACCACCCTC | ATCTCCACCA | CGTCCCACCT | 180 |
| TCCTCGCCCG | TTTCACATTC | CCAATAACCT | CCACTTCCCA | TAAACGACAC | CGTCTCCACA | 240 |
| TCTCCAACGT | CCTCTCCGAC | TCCAAACCCA | CCATCACCCA | TTCACCATTA | CCAACCGAAT | 300 |
| CATTTATCTC | CCGTTACGCT | CCAGACCAAC | CAAGAAAAGG | CGCTGATGTT | CTCGTCGAAG | 360 |
| CTCTGGAACG | TGAAGGCGTT | ACAGACGTCT | TCGCTTACCC | AGGTGGTGCC | TCCATGGAGA | 420 |
| TCCACCAAGC | TCTCACGCGC | TCAACCACCA | TCCGCAACGT | TCTCCCACGT | CACGAACAGG | 480 |
| GCGGCGTCTT | TGCTGCCGAA | GGCTACGCAC | GTGCCTCCGG | TCTTCCCGGC | GTCTGTATTG | 540 |
| CAACCTCTGG | TCCTGGAGCT | ACGAACCTAG | TAAGTGGTCT | TGCTGATGCT | TTATTAGACA | 600 |
| GTGTTCCAAT | GGTTGCTATT | ACTGGTCAAG | TTCCCAGGAG | AATGATTGGA | ACAGATGCGT | 660 |
| TTCAAGAAAC | CCCTATTGTT | GAGGTAACAC | GTTCCATTAC | TAAGCATAAT | TATTTAGTTT | 720 |
| TGGATGTCGA | GGATATTCCC | AGGATTGTTA | GGGAAGCTTT | TTATCTTGCG | TCTTCTGGTC | 780 |
| GACCCGGACC | GGTTTTAATT | GATGTACCTA | AGGATATACA | GCAGCAGTTG | GTAGTGCCTA | 840 |
| AATGGGATGA | GCCTATTAGG | TTACCTGGGT | ATTTGTCTAG | GTTGCCTAAA | ACGGAGAATA | 900 |
| ATGGGCAGTT | GGAACACATT | GTTAGGTTGG | TGAGTGAGGC | CAAGAGGCCG | GTTTTGTATG | 960 |
| TGGGGGGTGG | GTGTTTGAAT | TCGGGAGATG | AGTTGAGGCG | GTTTGTGGAG | CTTACGGGGA | 1020 |
| TACCGGTTGC | GAGTACGTTG | ATGGGGCTTG | GAGCGTACCC | TGCTTCTAGT | GATTTGTCGC | 1080 |
| TGCATATGCT | TGGGATGCAT | GGGACGGTTT | ATGCGAATTA | TGCGGTTGAT | AAGAGTGATT | 1140 |
| TGTTGCTTGC | GTTTGGGGTA | AGGTTTGATG | ACCGTGTGAC | GGGGAAGCTT | GAGGCTTTTG | 1200 |
| CTAGCAGAGC | TAAGATTGTT | CATATTGATA | TTGATTCTGC | GGAAATTGGG | AAGAATAAGC | 1260 |
| AGCCTCATGT | GTCGATTTGT | GGTGATATCA | AGGTCGCGTT | ACAGGGTCTG | AACAAGATTT | 1320 |
| TGGAGGTAAA | GAATTCGGTG | ACTAATCTTG | ATTTCTCGAA | CTGGAGGAAG | GAATTGGATG | 1380 |
| AGCAAAAGGT | TAAGTATCCG | TTGAGTTTTA | AACATTTGG | CGAAGCTATT | CCTCCGCAGT | 1440 |
| ATGCCATTCA | AGTGCTTGAT | GAGTTAACGG | GTGGGAATGC | GATTATTAGC | ACTGGGGTCG | 1500 |
| GGCAGCATCA | GATGTGGGCT | GCTCAGTTTT | ACAAATACAA | CAAGCCTAGA | CAATGGCTGA | 1560 |
| CGTCAGGTGG | ACTAGGCGCG | ATGGGTTTTG | GGTTGCCCGC | TGCTATCGGG | GCGGCTGTTG | 1620 |
| CAAGACCTGA | TGCGGTAGTA | GTTGATATCG | ATGGTGATGG | AAGCTTTATA | ATGAGCGTTC | 1680 |
| AAGAGTTAGC | CACAATCCGT | GTTGAAAATC | TTCCTGTTAA | GATTTGTTA | CTTAACAATC | 1740 |
| AGCATTTGGG | TATGGTGGTT | CAGTTGGAGG | ATCGGTTTTA | CAAGGCGAAT | CGGGCTCATA | 1800 |
| CCTACTTAGG | AAATCCGTCA | AAAGAGTCTG | AAATATTCCC | TAACATGTTG | AAGTTTGCTG | 1860 |
| AAGCGTGTGA | TATCCCAGCT | GCCCGAGTGA | CCCGGAAGGC | AGATCTACGA | GCAGCTATTC | 1920 |
| AGAAGATGTT | GGATACACCG | GGGCCTTACT | TGTTGGATGT | GATCGTGCCC | CATCAAGAAC | 1980 |
| ATGTGTTGCC | CATGATCCCG | GCTGGTGGAG | GTTTCATGGA | TGTGATCACC | GAAGGCGACG | 2040 |
| GCAGAATGAA | ATATTGAGCT | TCAATGTCAC | ATATAGTGTG | TTCTGTAAGC | AGTTTGTCGG | 2100 |
| TTATGAAGTT | AAATGTTTTG | TTGTGTAATT | TCGTTCCTGG | TTAAAAAATC | AAGCTT | 2156 |

( 2 ) INFORMATION FOR SEQ ID NO:4:

( i ) SEQUENCE CHARACTERISTICS:
        ( A ) LENGTH: 648 amino acids
        ( B ) TYPE: amino acid
        ( C ) STRANDEDNESS: single (D) TOPOLOGY: unknown (ii) MOLECULE TYPE: Protein (xi) SEQUENCE DESCRIPTION: SEQ ID NO:4:

| Met | Ala | Ala | Ile | Pro | His | Thr | Asn | Pro | Ser | Ile | Thr | Thr | Lys | Pro | Pro |
|---|---|---|---|---|---|---|---|---|---|---|---|---|---|---|---|
| 1 | | | | 5 | | | | | 10 | | | | | 15 | |

| Ser | Ser | Pro | Pro | Arg | Pro | Thr | Phe | Leu | Ala | Arg | Phe | Thr | Phe | Pro | Ile |
|---|---|---|---|---|---|---|---|---|---|---|---|---|---|---|---|
| | | | 20 | | | | 25 | | | | | 30 | | | |

| Thr | Ser | Thr | Ser | His | Lys | Arg | His | Arg | Leu | His | Ile | Ser | Asn | Val | Leu |
|---|---|---|---|---|---|---|---|---|---|---|---|---|---|---|---|
| | | 35 | | | | | 40 | | | | | 45 | | | |

| Ser | Asp | Ser | Lys | Pro | Thr | Ile | Thr | His | Ser | Pro | Leu | Pro | Thr | Lys | Ser |
|---|---|---|---|---|---|---|---|---|---|---|---|---|---|---|---|
| | 50 | | | | | 55 | | | | | 60 | | | | |

| Phe | Ile | Ser | Arg | Tyr | Ala | Pro | Asp | Gln | Pro | Arg | Lys | Gly | Ala | Asp | Val |
|---|---|---|---|---|---|---|---|---|---|---|---|---|---|---|---|
| 65 | | | | 70 | | | | | 75 | | | | | 80 | |

| Leu | Val | Glu | Ala | Leu | Glu | Arg | Glu | Gly | Val | Thr | Asp | Val | Phe | Ala | Tyr |
|---|---|---|---|---|---|---|---|---|---|---|---|---|---|---|---|
| | | | | 85 | | | | | 90 | | | | | 95 | |

| Pro | Gly | Gly | Ala | Ser | Met | Glu | Ile | His | Gln | Ala | Leu | Thr | Arg | Ser | Thr |
|---|---|---|---|---|---|---|---|---|---|---|---|---|---|---|---|
| | | | 100 | | | | | 105 | | | | | 110 | | |

| Thr | Ile | Arg | Asn | Val | Leu | Pro | Arg | His | Glu | Gln | Gly | Gly | Val | Phe | Ala |
|---|---|---|---|---|---|---|---|---|---|---|---|---|---|---|---|
| | | | 115 | | | | | 120 | | | | | 125 | | |

| Ala | Glu | Gly | Tyr | Ala | Arg | Ala | Ser | Gly | Leu | Pro | Gly | Val | Cys | Ile | Ala |
|---|---|---|---|---|---|---|---|---|---|---|---|---|---|---|---|
| | 130 | | | | | 135 | | | | | 140 | | | | |

| Thr | Ser | Gly | Pro | Gly | Ala | Thr | Asn | Leu | Val | Ser | Gly | Leu | Ala | Asp | Ala |
|---|---|---|---|---|---|---|---|---|---|---|---|---|---|---|---|
| 145 | | | | | 150 | | | | | 155 | | | | | 160 |

| Leu | Leu | Asp | Ser | Val | Pro | Met | Val | Ala | Ile | Thr | Gly | Gln | Val | Pro | Arg |
|---|---|---|---|---|---|---|---|---|---|---|---|---|---|---|---|
| | | | | 165 | | | | | 170 | | | | | 175 | |

| Arg | Met | Ile | Gly | Thr | Asp | Ala | Phe | Gln | Glu | Thr | Pro | Ile | Val | Glu | Val |
|---|---|---|---|---|---|---|---|---|---|---|---|---|---|---|---|
| | | | 180 | | | | | 185 | | | | | 190 | | |

| Thr | Arg | Ser | Ile | Thr | Lys | His | Asn | Tyr | Leu | Val | Leu | Asp | Val | Glu | Asp |
|---|---|---|---|---|---|---|---|---|---|---|---|---|---|---|---|
| | | 195 | | | | | 200 | | | | | 205 | | | |

| Ile | Pro | Arg | Ile | Val | Arg | Glu | Ala | Phe | Tyr | Leu | Ala | Ser | Ser | Gly | Arg |
|---|---|---|---|---|---|---|---|---|---|---|---|---|---|---|---|
| | 210 | | | | | 215 | | | | | 220 | | | | |

| Pro | Gly | Pro | Val | Leu | Ile | Asp | Val | Pro | Lys | Asp | Ile | Gln | Gln | Gln | Leu |
|---|---|---|---|---|---|---|---|---|---|---|---|---|---|---|---|
| 225 | | | | | 230 | | | | | 235 | | | | | 240 |

| Val | Val | Pro | Lys | Trp | Asp | Glu | Pro | Ile | Arg | Leu | Pro | Gly | Tyr | Leu | Ser |
|---|---|---|---|---|---|---|---|---|---|---|---|---|---|---|---|
| | | | | 245 | | | | | 250 | | | | | 255 | |

| Arg | Phe | Pro | Lys | Thr | Glu | Asn | Asn | Gly | Gln | Leu | Glu | Gln | Ile | Val | Arg |
|---|---|---|---|---|---|---|---|---|---|---|---|---|---|---|---|
| | | | 260 | | | | | 265 | | | | | 270 | | |

| Leu | Val | Ser | Glu | Ala | Lys | Arg | Pro | Val | Leu | Tyr | Val | Gly | Gly | Gly | Cys |
|---|---|---|---|---|---|---|---|---|---|---|---|---|---|---|---|
| | | 275 | | | | | 280 | | | | | 285 | | | |

| Leu | Asn | Ser | Gly | Asp | Glu | Leu | Arg | Arg | Phe | Val | Glu | Leu | Thr | Gly | Ile |
|---|---|---|---|---|---|---|---|---|---|---|---|---|---|---|---|
| | 290 | | | | | 295 | | | | | 300 | | | | |

| Pro | Val | Ala | Ser | Thr | Leu | Met | Gly | Leu | Gly | Ala | Tyr | Pro | Ala | Ser | Ser |
|---|---|---|---|---|---|---|---|---|---|---|---|---|---|---|---|
| 305 | | | | | 310 | | | | | 315 | | | | | 320 |

| Asp | Leu | Ser | Leu | His | Met | Leu | Gly | Met | His | Gly | Thr | Val | Tyr | Ala | Asn |
|---|---|---|---|---|---|---|---|---|---|---|---|---|---|---|---|
| | | | | 325 | | | | | 330 | | | | | 335 | |

| Tyr | Ala | Val | Asp | Lys | Ser | Asp | Leu | Leu | Ala | Phe | Gly | Val | Arg | Phe |
|---|---|---|---|---|---|---|---|---|---|---|---|---|---|---|
| | | | 340 | | | | | 345 | | | | | 350 | |

| Asp | Asp | Arg | Val | Thr | Gly | Lys | Leu | Glu | Ala | Phe | Ala | Ser | Arg | Ala | Lys |
|---|---|---|---|---|---|---|---|---|---|---|---|---|---|---|---|
| | | 355 | | | | | 360 | | | | | 365 | | | |

| Ile | Val | His | Ile | Asp | Ile | Asp | Ser | Ala | Glu | Ile | Gly | Lys | Asn | Lys | Gln |
|---|---|---|---|---|---|---|---|---|---|---|---|---|---|---|---|
| | 370 | | | | | 375 | | | | | 380 | | | | |

| Pro | His | Val | Ser | Ile | Cys | Gly | Asp | Ile | Lys | Val | Ala | Leu | Gln | Gly | Leu |
|---|---|---|---|---|---|---|---|---|---|---|---|---|---|---|---|
| 385 | | | | | 390 | | | | | 395 | | | | | 400 |

```
Asn  Lys  Ile  Leu  Glu  Val  Lys  Asn  Ser  Val  Thr  Asn  Leu  Asp  Phe  Ser
               405                 410                      415

Asn  Trp  Arg  Lys  Glu  Leu  Asp  Glu  Gln  Lys  Val  Lys  Tyr  Pro  Leu  Ser
               420                 425                      430

Phe  Lys  Thr  Phe  Gly  Glu  Ala  Ile  Pro  Pro  Gln  Tyr  Ala  Ile  Gln  Val
          435                      440                      445

Leu  Asp  Glu  Leu  Thr  Gly  Gly  Asn  Ala  Ile  Ile  Ser  Thr  Gly  Val  Gly
     450                      455                 460

Gln  His  Gln  Met  Trp  Ala  Ala  Gln  Phe  Tyr  Lys  Tyr  Asn  Lys  Pro  Arg
465                      470                 475                           480

Gln  Trp  Leu  Thr  Ser  Gly  Gly  Leu  Gly  Ala  Met  Gly  Phe  Gly  Leu  Pro
                    485                      490                      495

Ala  Ala  Ile  Gly  Ala  Ala  Val  Ala  Arg  Pro  Asp  Ala  Val  Val  Val  Asp
               500                      505                      510

Ile  Asp  Gly  Asp  Gly  Ser  Phe  Ile  Met  Asn  Val  Gln  Glu  Leu  Ala  Thr
          515                      520                 525

Ile  Arg  Val  Glu  Asn  Leu  Pro  Val  Lys  Ile  Leu  Leu  Leu  Asn  Asn  Gln
     530                      535                      540

His  Leu  Gly  Met  Val  Val  Gln  Trp  Glu  Asp  Arg  Phe  Tyr  Lys  Ala  Asn
545                      550                      555                      560

Arg  Ala  His  Thr  Tyr  Leu  Gly  Asn  Pro  Ser  Lys  Glu  Ser  Glu  Ile  Phe
                    565                      570                      575

Pro  Asn  Met  Leu  Lys  Phe  Ala  Glu  Ala  Cys  Asp  Ile  Pro  Ala  Ala  Arg
               580                      585                      590

Val  Thr  Arg  Lys  Ala  Asp  Leu  Arg  Ala  Ala  Ile  Gln  Lys  Met  Leu  Asp
          595                      600                 605

Thr  Pro  Gly  Pro  Tyr  Leu  Leu  Asp  Val  Ile  Val  Pro  His  Gln  Glu  His
     610                      615                      620

Val  Leu  Pro  Met  Ile  Pro  Ala  Gly  Gly  Gly  Phe  Met  Asp  Val  Ile  Thr
625                      630                      635                      640

Glu  Gly  Asp  Gly  Arg  Met  Lys  Tyr
                    645
```

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:5:

```
Met  Leu  Gly  Met  His  Gly
1                   5
```

( 2 ) INFORMATION FOR SEQ ID NO:6:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:6:

```
ATGCTTACTG  GGACTGATGC  ACTGG                                    25
```

( 2 ) INFORMATION FOR SEQ ID NO:7:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:7:

```
Val Ala Leu Gly Leu Tyr Gly Leu Asn His Ile Ser Gly Leu Asn Met
 1               5                  10                  15
Glu Thr Thr Arg Pro Pro His Glu
                20
```

( 2 ) INFORMATION FOR SEQ ID NO:8:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:8:

```
GTACGTGGCA GTCAAGCACT CAAGATGT                                          28
```

( 2 ) INFORMATION FOR SEQ ID NO:9:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:9:

```
ACATCTTGAG TGCTTGACTG CCACGTAC                                          28
```

( 2 ) INFORMATION FOR SEQ ID NO:10:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:10:

```
GTTCAGCCTG GTTAAGTCCA AGC                                               23
```

( 2 ) INFORMATION FOR SEQ ID NO:11:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:11:

```
GAGTATTCTTTCCAGGGTAAAAAGC                                               25
```

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:12:

GGCGAAGCTA TTCCTCCG                             18

( 2 ) INFORMATION FOR SEQ ID NO:13:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:13:

ATTAACCCTC ACTAAAG                              17

( 2 ) INFORMATION FOR SEQ ID NO:14:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:14:

AAATACGACT CACTATAG                            18

( 2 ) INFORMATION FOR SEQ ID NO:15:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:15:

CGGAGGAATA GCTTCGCC                            18

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:16:

GGCGAAGCTA TTCCTCCG                             18

( 2 ) INFORMATION FOR SEQ ID NO:17:

( i ) SEQUENCE CHARACTERISTICS:
        ( A ) LENGTH: 21 base pairs
        ( B ) TYPE: nucleic acid ( C ) STRANDEDNESS: single
            ( D ) TOPOLOGY: linear ( i i ) MOLECULE TYPE: oligonucleotide ( x i ) SEQUENCE DESCRIPTION: SEQ ID NO:17:

CGGTTTGTGG AGCTTACGGG G                                                21

( 2 ) INFORMATION FOR SEQ ID NO:18:

( i ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: linear ( i i ) MOLECULE TYPE: oligonucleotide ( x i ) SEQUENCE DESCRIPTION: SEQ ID NO:18:

GCAGCTATTC AGAGAATGTT GG                                               22

( 2 ) INFORMATION FOR SEQ ID NO:19:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: oligonucleotide ( x i ) SEQUENCE DESCRIPTION: SEQ ID NO:19:

CAATATTCAT TCTGCCGTCG                                                  20

( 2 ) INFORMATION FOR SEQ ID NO:20:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: oligonucleotide ( x i ) SEQUENCE DESCRIPTION: SEQ ID NO:20:

CTTCATAACC GACAAACTGC                                                  20

( 2 ) INFORMATION FOR SEQ ID NO:21:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: oligonucleotide ( x i ) SEQUENCE DESCRIPTION: SEQ ID NO:21:

GTCTGTATTG CAACCTCTGG                                                  20

( 2 ) INFORMATION FOR SEQ ID NO:22:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( i i ) MOLECULE TYPE: oligonucleotide ( x i ) SEQUENCE DESCRIPTION: SEQ ID NO:22:

CAATCCTGGG AATATCC                                17

( 2 ) INFORMATION FOR SEQ ID NO:23:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: oligonucleotide ( x i ) SEQUENCE DESCRIPTION: SEQ ID NO:23:

GTAGCTCCAG GACCAGAGG                              19

( 2 ) INFORMATION FOR SEQ ID NO:24:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: oligonucleotide ( x i ) SEQUENCE DESCRIPTION: SEQ ID NO:24:

CATTCAACAA TGGCGGCCAT CC                          22

( 2 ) INFORMATION FOR SEQ ID NO:25:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: oligonucleotide ( x i ) SEQUENCE DESCRIPTION: SEQ ID NO:25:

GCATAATTCG CATAAACGGT CCC                         23

( 2 ) INFORMATION FOR SEQ ID NO:26:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: oligonucleotide ( x i ) SEQUENCE DESCRIPTION: SEQ ID NO:26:

CAGCAAACTT CAACATGTTA GGG                         23